US010226364B2

(12) United States Patent
Radspieler

(10) Patent No.: US 10,226,364 B2
(45) Date of Patent: Mar. 12, 2019

(54) PROSTHESIS SOCKET WITH INSERTION AID

(71) Applicant: OTTO BOCK HEALTHCARE GMBH, Duderstadt (DE)

(72) Inventor: Andreas Radspieler, Neubeuern (DE)

(73) Assignee: OTTO BOCK HEALTHCARE GMBH, Duderstadt (DE)

(*) Notice: Subject to any disclaimer, the term of this patent is extended or adjusted under 35 U.S.C. 154(b) by 0 days.

(21) Appl. No.: 14/911,528

(22) PCT Filed: Aug. 12, 2014

(86) PCT No.: PCT/EP2014/002207
§ 371 (c)(1),
(2) Date: Feb. 11, 2016

(87) PCT Pub. No.: WO2015/022069
PCT Pub. Date: Feb. 19, 2015

(65) Prior Publication Data
US 2016/0184112 A1 Jun. 30, 2016

(30) Foreign Application Priority Data
Aug. 12, 2013 (DE) .................. 10 2013 013 314

(51) Int. Cl.
A61F 2/78 (2006.01)
A61F 2/80 (2006.01)
(Continued)

(52) U.S. Cl.
CPC .......... A61F 2/7812 (2013.01); A61F 2/7843 (2013.01); A61F 2/80 (2013.01);
(Continued)

(58) Field of Classification Search
CPC ................... A61F 2/7812; A61F 2002/7818
See application file for complete search history.

(56) References Cited

U.S. PATENT DOCUMENTS 5,211,667 A 5/1993 Danforth
2004/0098136 A1* 5/2004 Caspers ................ A61F 2/5046
623/34
(Continued)

FOREIGN PATENT DOCUMENTS

DE 20217525 U1 2/2003
DE 102011105488 A1 12/2012
(Continued)

OTHER PUBLICATIONS

PCT International Search Report for PCT International Patent Application No. PCT/EP2014/002207, dated Oct. 9, 2014.

Primary Examiner — David H Willse
(74) Attorney, Agent, or Firm — Holland & Hart

(57) ABSTRACT

A prosthesis stem includes a stem body for receiving an amputation stump and an insertion aid apparatus, which facilitates the insertion of the amputation stump into the stem body, wherein the insertion aid apparatus comprises an insertion inlay which is connected in the proximal edge region thereof to a holding apparatus which is fixed to the stem body. The insertion inlay has an insertion stocking, which is movable between an outer position, in which the insertion inlay is at least partially located outside of the stem body, and an inner position, in which the insertion stocking covers the stem body.

19 Claims, 4 Drawing Sheets

(51) Int. Cl.
*A61F 2/74* (2006.01)
*A61F 2/50* (2006.01)

(52) U.S. Cl.
CPC . *A61F 2002/501* (2013.01); *A61F 2002/5007* (2013.01); *A61F 2002/747* (2013.01); *A61F 2002/7818* (2013.01); *A61F 2002/7831* (2013.01); *A61F 2002/7837* (2013.01); *A61F 2002/7862* (2013.01); *A61F 2002/7868* (2013.01); *A61F 2002/802* (2013.01)

(56) References Cited

U.S. PATENT DOCUMENTS

| | | |
|---|---|---|
| 2005/0240283 A1 | 10/2005 | Kania |
| 2010/0249950 A1 | 9/2010 | Bielefeld |
| 2015/0289999 A1 | 10/2015 | Radspieler |

FOREIGN PATENT DOCUMENTS

| | | |
|---|---|---|
| DE | 102012022414 A1 | 5/2014 |
| GB | 1086560 | 10/1967 |
| WO | 2007107800 A2 | 9/2007 |
| WO | 2009062489 A1 | 5/2009 |
| WO | 2014075808 A2 | 5/2014 |

\* cited by examiner

PROSTHESIS SOCKET WITH INSERTION AID

TECHNICAL FIELD

The invention relates to a prosthesis socket with a socket body for receiving an amputation stump and with an insertion aid which facilitates the insertion of the amputation stump into the socket body.

BACKGROUND

In the case of arm and leg prostheses, various possible ways are known for putting the prosthesis on and for taking it off. In the case of liner systems, a liner (compression stocking) is initially turned inside out and pulled over the amputation stump or rolled onto the latter. This is initially done entirely independently of and separate from the prosthesis socket. The liner in this case sits tightly on the amputation stump in such a way that a compression of the amputation stump is achieved. Furthermore, liners of this kind can be provided with a fixing pin at their distal end in order to lock the liner to the prosthesis socket once the amputation stump has been inserted into the prosthesis socket. The liner sits firmly on the amputation stump as a result of the gas tightness and frictional adhesion.

A prosthesis socket of this kind is known from WO 2009/062489 A1. The prosthesis socket described there can in addition also have a connection in the socket body in order to attach a vacuum pump and, as a result, increase the vacuum between socket body and liner.

DE 10 2011 105 488 A1 relates to a device for securing a prosthesis to intact parts of the body by means of an underpressure between a liner unit, pulled over the stump, and a prosthesis socket enclosing the stump. The liner unit has a first liner, facing toward the stump, and a second liner which is arranged on the outside and protrudes beyond the edge of the prosthesis socket. The protruding area of the second liner is configured such that, after being turned back over the edge of the prosthesis socket, it adheres to the outside of the prosthesis socket and produces an airtight connection.

DE 202 17 525 U1 relates to a means for putting on prosthesis sockets, for example, said means having at least two sleeves lying one inside the other, wherein the inner sleeve is turned back into the outer sleeve for putting on the prosthesis socket. The two sleeves are connected to each other at a first end. At the second end, gripping means are provided on the inner sleeve, while the outer sleeve has a passage through which the gripping means can be reached from the outside.

DE 10 2012 022 414 A1 relates to a prosthesis socket with a socket body into which a stump can be inserted, and with a flexible inlay which is arranged between the socket body and the stump when the prosthesis socket is in place. The inlay, together with the socket body, defines a fluid pressure chamber which is connected to an overpressure generator and which is designed to be airtight in such a way that, by generation of an overpressure in the fluid pressure chamber, a displacement force acting in the proximal direction is exerted on an end area of the inlay, so as to facilitate the removal of the prosthesis socket.

In liner systems, it is also known for an insertion aid in the form of a cord to be secured, instead of a fixing pin, at the distal end of the liner, which cord is pulled through an opening in the socket bottom and can be fixed by means of a cable clip. To take the prosthesis off, the latch mechanism of the locking pin or the cable clip is unlocked and the prosthesis socket is removed from the stump.

However, a disadvantage of the known prosthesis sockets is that the putting on and taking off of the prosthesis is possible only by applying considerable force. To utilize a prosthesis socket in an optimum manner, it should sit as tightly as possible on the amputation stump. The tighter the amputation stump sits on the prosthesis socket, the more difficult it is, however, to put on and take off the prosthesis. Although liners make it easier to insert the amputation stump into the prosthesis socket, they have the disadvantage that they first have to be pulled over the amputation stump by applying considerable force. This entails considerable problems particularly for weak, elderly and injured persons, and also for persons who have had an arm amputated.

SUMMARY

The object of the invention is therefore to create a prosthesis socket which is of the type mentioned at the outset and which in particular makes it easier to put on a prosthesis.

According to the invention, this object is achieved by a prosthesis socket having the features disclosed herein.

In the case of the prosthesis socket according to the invention, the insertion aid comprises an insertion inlay which, in the proximal edge area thereof, is connected to a holding device which is fixed on the socket body. Moreover, the insertion inlay has an insertion stocking, which is movable between an outer position, in which the insertion inlay is located at least in part, preferably for the most part, outside the socket body, and an inner position, in which the insertion stocking lines the socket body.

Advantageously, the insertion inlay has elastic, pressure-stable stretching elements which extend along the insertion stocking, are fixed on the latter and are movable together with the insertion stocking. When the prosthesis socket is being taken off, these stretching elements have the purpose of ensuring that a pressure which is exerted on the distal end of the insertion inlay, for example by compressed air, is conveyed onward in the proximal direction. It is thereby possible to easily remove an amputation stump from the insertion inlay without causing bruising of soft-tissue parts. Moreover, creasing of the insertion inlay is avoided or at least greatly reduced.

The stretching elements therefore need to be so stable under pressure that they are able to convey the pressure, applied for example at their distal end, onward to their proximal end. However, they require a certain flexibility in order to be able to adapt to and follow the resulting changing contour of the insertion inlay, and in particular of the insertion stocking, as the prosthesis socket is taken off. It is advantageous here if this bending or flexion of the individual stretching elements, which occurs during removal, can be performed without buckling or bending of the stretching elements. The latter are therefore also described below as being resistant to buckling.

The holding device is preferably movable relative to the proximal socket edge of the socket body. Particularly in combination with elastic, pressure-stable stretching elements, this has the effect that, when the prosthesis socket is being taken off and the amputation stump removed from the insertion stocking, said insertion stocking is widened, and with it the insertion inlay, such that the amputation stump can be easily removed and, subsequently, can once again be easily introduced into the insertion inlay.

The holding device is preferably fixed on the outer wall of the socket body. It is particularly preferably fixed by its distal end.

The insertion inlay according to the invention makes it much easier to insert the amputation stump into the socket body. It is no longer necessary to pull a liner onto the amputation stump prior to the insertion procedure. Before the amputation stump is inserted into the socket body, the insertion inlay extends proximally beyond the proximal socket edge, the proximal portion of the insertion inlay being stretched farther radially outward and widened by the stretching elements, in such a way that the amputation stump can be easily placed onto the insertion inlay. During the further insertion of the amputation stump into the socket body, the insertion inlay slides along the socket body in the distal direction, until the amputation stump rests on the bottom of the prosthesis socket. In this insertion procedure, the amputation stump is compressed in the desired manner in accordance with the reduced diameter of the socket body. The insertion procedure can be assisted, if appropriate, by means of a winch, with which the insertion inlay or a further socket inlay, which is located between the insertion inlay and the socket body, is pulled in the distal direction. During the insertion procedure, the stretching elements ensure that the elastic, extensible insertion stocking enters the socket body without creasing and ultimately lines this socket body.

The insertion inlay according to the invention is particularly advantageous in combination with a reversible socket inlay which is arranged between the insertion inlay, located in its inner position, and the socket body, which socket inlay delimits, on its own or together with the socket body, a fluid-tight fluid pressure chamber, such that the socket inlay can be pushed up in the proximal direction by generation of an overpressure in the fluid pressure chamber. The reversing procedure is expediently effected by means of compressed air. The amputation stump is in this case pressed out of the socket body by the fluid. In this way, the removal of the amputation stump from the prosthesis socket is greatly facilitated. To ensure that the reversing procedure takes place uniformly and symmetrically, this socket inlay must be secured on the socket body in a socket entry plane which is arranged perpendicularly with respect to the stump insertion direction. However, the rigid socket body generally extends beyond this socket entry plane and, on the other side (proximally) of the socket entry plane, is no longer lined by the socket inlay. The insertion inlay, which also extends over the proximal edge area of the socket body, reduces very considerably the friction in the proximal edge area of the socket body during the insertion of the amputation stump. Pain caused by pulling of the skin and compression of the soft-tissue parts above the proximal edge area of the socket body can be substantially reduced.

A further advantage of the insertion inlay according to the invention is that, at the start of the insertion procedure, a support platform for the amputation stump is always created that lies perpendicularly with respect to the insertion direction. If the insertion direction is vertical, this support platform thus lies in a horizontal plane. This is also the case if the proximal socket edge extends, in the normal manner, obliquely and in an undulating manner. The holding device, movable relative to the proximal socket edge, ensures that the insertion inlay is stretched beyond the proximal socket edge in the desired manner, in particular in an umbrella shape or mushroom shape, when the insertion inlay is brought to its outer position.

Advantageously, the holding device is fixed on the socket body at the height of a socket entry plane which lies perpendicularly with respect to the stump insertion direction. This ensures that, on account of the different connection lengths of the holding device, which are caused by the oblique or undulating edge profile of the socket body and are generally shorter medially than laterally, the insertion inlay is turned back such that medially and laterally, and also anteriorly and posteriorly, substantial outward bulges, if appropriate also of different sizes, of the insertion inlay can occur such that the insertion inlay is stretched without forming creases.

The holding device is expediently composed of a plurality of holding tapes or cords arranged about the circumference of the socket body. These holding tapes or cords can be inelastic or elastic. Alternatively, it is also possible that the holding device is composed of a hose-like holding member that surrounds the socket body. The holding tapes or cords are each advantageously secured on a stretching element. Alternatively, however, they can also be secured at the proximal edge of the insertion stocking.

Advantageously, the stretching elements are composed of elongate, flexible guide rods or slats, which are firmly connected to the insertion stocking, for example glued or injected on directly, or are fitted in guide tabs or pockets of the insertion stocking.

Advantageously, a plurality of stretching elements are arranged about the circumference of the insertion stocking, with an at least approximately identical spacing between them. However, the number and arrangement of the stretching elements can be varied and adapted to the geometric circumstances and to the material of the insertion stocking.

Advantageously, the stretching elements extend from the bottom of the insertion stocking to the proximal edge area of the latter. In this way, a compression of the insertion stocking upon conversion to its outer position is prevented in a particularly effective manner.

Advantageously, the insertion inlay, in its outer position, is at least for the most part inverted, wherein the bottom of the insertion stocking is located outside the socket body or at the same height as the farthest proximally protruding socket edge. This permits particularly simple attachment and insertion of the amputation stump into the prosthesis socket.

According to an advantageous embodiment, a flexible socket inlay is arranged between the insertion inlay, located in its inner position, and the socket body, which flexible socket inlay delimits, on its own or together with the socket body, a fluid-tight fluid pressure chamber, can be pushed out in the proximal direction by generation of an overpressure in the fluid pressure chamber and has a bottom movable relative to the socket body, wherein the insertion inlay is connected to the socket inlay in the area of the bottom. In this embodiment, the insertion inlay can be pressed proximally outward by the socket inlay by means of fluid, in particular by means of compressed air, and can be inverted mushroom-like to a larger circumference outside the socket body. The stretching elements in this case bend radially outward like springs on account of their being secured to the holding device and in so doing they stretch the insertion inlay in circumference, wherein the latter is turned back like an umbrella or mushroom.

Advantageously, the stretching elements are made from plastic, for example PU, PE, PP, a fiber-reinforced plastic or silicone, copolymers or similar materials, or from spring steel.

Advantageously, the bottom of the socket inlay is designed as a dimensionally stable cap. Such a cap has the effect that the reversing procedure takes place in a proper and uniform manner along the prosthesis socket. Moreover, with the inlay turned out, the cap creates a shell-like depression for fitting the amputation stump, which permits full contact with the distal end face of the amputation stump.

Advantageously, the socket inlay is connected in an airtight manner to the socket body in a socket entry plane that lies perpendicularly with respect to the stump insertion direction. In this embodiment, a single layer of the socket inlay is arranged between the insertion inlay, located in the inner position, and the socket body, which socket inlay, together with the socket body, delimits the fluid pressure chamber. As an alternative to this, however, it is also possible to design the socket inlay as a fluid-tight bladder, of which the two halves are turned into each other and are arranged in the intermediate space between socket body and insertion inlay. To turn the socket inlay outward, fluid is then introduced into the interior of the inlay bladder. In this embodiment, it is not necessary to seal off the socket inlay with respect to the socket body.

Advantageously, the prosthesis socket has at least one tensioning element, by means of which a distal end of the insertion inlay is movable in the direction of a distal end of the socket body. This tensioning element can be, for example, the aforementioned cable, which is movable via a winch. However, embodiments are also conceivable in which, for example, a cable is actuated by hand in order to be able to introduce the insertion inlay into the socket body. A particularly convenient option is for a deflecting roller or some other deflector to be provided at the distal end of the socket body so as to deflect the tensioning element. It is thus possible for the person wearing the prosthesis and the prosthesis socket to pull the tensioning element upward, i.e. in the proximal direction, in order to be able to introduce the insertion inlay into the socket body. The tensioning element can be in particular a tensioning cable, a tensioning chain or a tensioning tape, wherein a tensioning chain and a tensioning tape have the advantage that they do not have to be wound up. A more compact configuration is thereby possible. A tensioning tape moreover has the advantage that it can be conveyed by a corresponding conveyor device. Of course, several tensioning elements are also conceivable, optionally of a different or identical configuration.

BRIEF DESCRIPTION OF THE DRAWINGS

The invention is explained in more detail below on the basis of examples and with reference to the drawings, in which.

DETAILED DESCRIPTION

Figure 1:
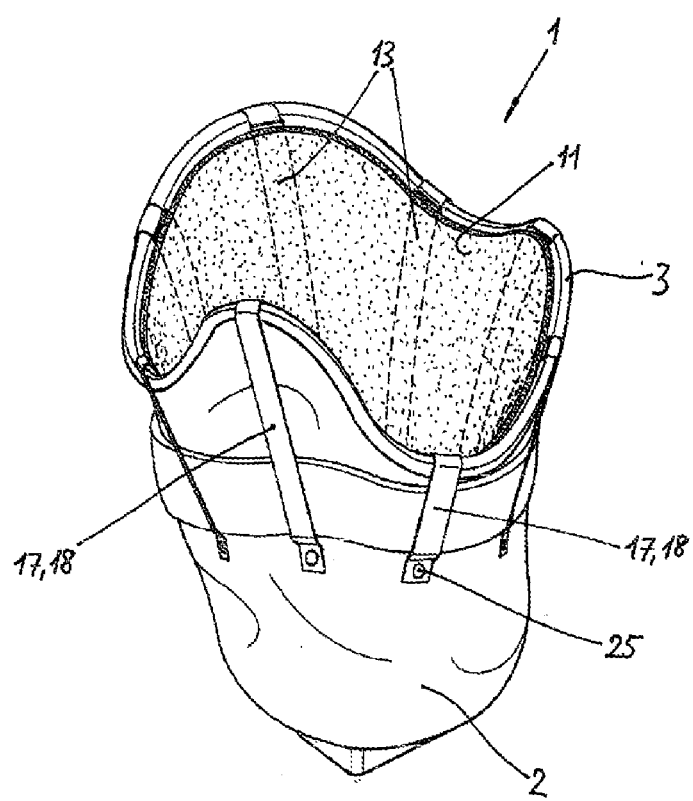
FIG. 1 shows a perspective view of the prosthesis socket according to the invention.

The figures show a prosthesis socket 1 for a prosthetic leg.

The prosthesis socket 1 comprises a bucket-shaped or bowl-shaped socket body 2 produced from rigid material, in particular from plastics material. At the proximal end, the socket body 2 has a proximal insertion opening 3 for the amputation stump 19 (indicated only in FIG. 4). At its distal end, the socket body 2 is at least substantially closed. The socket body 2 surrounds an interior 4.

The prosthesis socket 1 further comprises a flexible socket inlay 5 produced from an elastic material such as silicone, polyurethane, copolymer or similar materials. In the position of the socket inlay 5 shown in FIGS. 1 and 2, which corresponds to the position that is assumed with the amputation stump 19 inserted, the socket inlay 5 covers the socket body 2 in the entire region between a socket entry plane 20 and the bottom of the socket body 2. The socket inlay 5 thus serves, on the one hand, as cushioning and, on the other hand, as an elastic intermediate layer which allows force to be transmitted over a large area, and in a manner that is as free of pressure points as possible, between the amputation stump 19 and the socket body 2.

The socket entry plane 20 here designates the plane which lies perpendicularly with respect to the insertion direction 22 (FIG. 4) of the amputation stump 19 and which, in the illustrative embodiment shown, is arranged horizontally.

The socket inlay 5 is secured only in its proximal end area to a connection 6 which extends in a ring-shaped manner on the inside surface of the socket body 2 at the height of the socket entry plane 20. In the illustrative embodiment shown, this connection 6 is realized by a clamping ring 23 which extends in the circumferential direction of the socket body 2 and which is fitted into an outwardly curved bead 24 of the socket body 2 and generates a radial tensioning force toward the outside. The proximal end of the socket inlay 5 is firmly clamped inside the bead 24 by the clamping ring 23 and is sealed off in an airtight manner with respect to the socket body 2.

Instead of such a connection 6, other connections, for example adhesive connections, are also possible.

The socket inlay 5 is made of a fluid-tight, elastic and easily extensible material. The intermediate space between socket body 2 and socket inlay 5 is therefore sealed off in a fluid-tight manner. Moreover, in the areas remote from the connection 6, the socket inlay 5 bears only loosely on the inner surface of the socket body 2.

Moreover, in the distal end area of the prosthesis socket 1, there is an overpressure generator 28 which is fastened on the socket body 2 or can be brought into fluid communication with the latter. This overpressure generator 28 is connected via a fluid channel 8 to the intermediate space between the socket body 2 and the socket inlay 5 in order, when necessary, to pump fluid into this intermediate space and to generate an overpressure therein. This intermediate space thus constitutes a fluid pressure chamber, which is labeled by reference sign 9 in FIGS. 3 and 4. The fluid is preferably air, and the overpressure generator 28 is an electrically operated compressor, with which compressed air can be pumped into the fluid pressure chamber 9.

Figure 2:
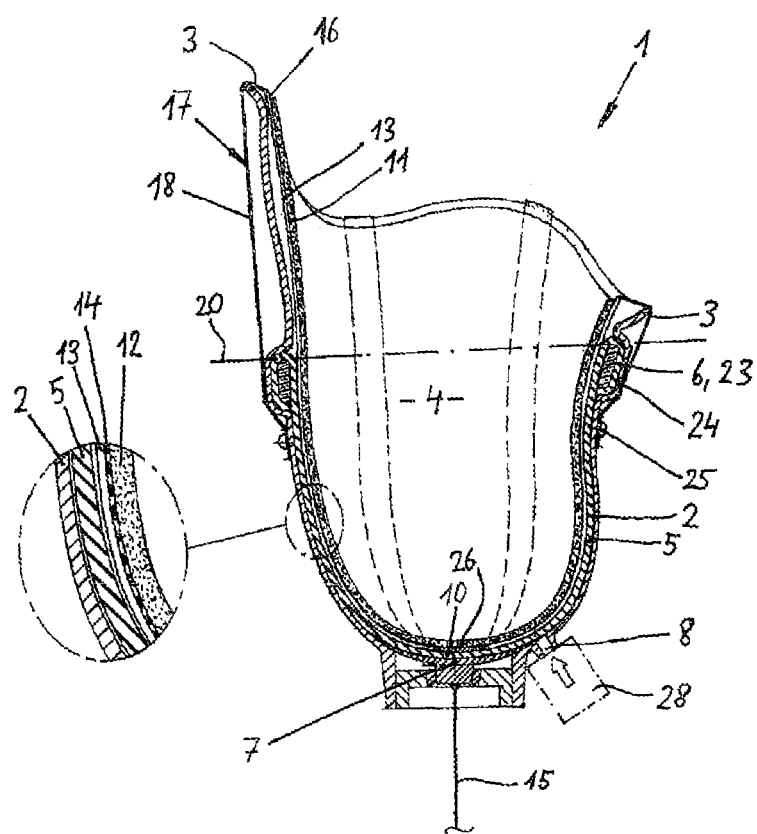
FIG. 2 shows a vertical section through the prosthesis socket from FIG. 1, with a detail being shown in enlarged form.

As a result of pumping fluid into the fluid pressure chamber 9, a displacement force acting in the proximal direction is exerted on a bottom 10 of the socket inlay 5, which in FIG. 2 is arranged in the area of the bottom of the socket body 2 and is reinforced on the outside with a dimensionally stable cap 7. This brings about a displacement of the bottom 10 in the proximal direction relative to the socket body 2. During this displacement, as can be seen from FIGS. 3 and 4, the socket inlay 5 is inverted, wherein the bottom 10 inside the side wall of the socket body 2 moves in the proximal direction at least as far as the farthest proximal socket edge 3 and, in the illustrative embodiment shown, even beyond this.

In order to prevent the socket inlay 5 from rotating about the longitudinal axis inside the socket body 2, anti-rotation elements, which comprise positive-locking webs and grooves extending between the webs in the longitudinal direction of the prosthesis socket 1, are provided, on the one hand, on the socket body 2 and, on the other hand, on the socket inlay 5. These anti-rotation elements are expediently arranged in the central and/or distal third of the prosthesis socket 1, since the socket inlay 5 is already prevented from twisting relative to the socket body 2 at the proximal end by the fluid-tight connection 6. In addition, the anti-rotation elements provided on the socket inlay 5 are flexible in order to permit the inversion of the socket inlay 5 even in the area of the anti-rotation elements.

Alternatively or in addition, it is also possible to provide corresponding anti-rotation elements between the bottom 10 of the socket inlay 5, or the cap 7, and the adjacent bottom of the socket body 2.

In order to be able to connect the prosthesis socket 1 in as simple a manner as possible to the amputation stump 19, a cable pull device is moreover provided which comprises a winch (not shown) and a cable 15 actuated by the latter. In a manner not shown, the winch is secured on the distal end of the socket body 2. Moreover, the cable 15 is guided through a cable feedthrough (not shown) which is sealed off from the fluid pressure chamber 9 and ensures that, upon generation of an overpressure in the fluid pressure chamber 9, the fluid cannot flow undesirably out via the cable feedthrough. This sealing can be effected, for example, by flexible sealing lips (not shown) which bear on the cable 15. Moreover, it may already suffice for the gap between cable 15 and cable feedthrough to be made so narrow that the amount of fluid passing through is negligible.

At its proximal end, the cable 15 is connected centrally to the bottom 10 of the socket inlay 5 or to the dimensionally stable cap 7. By virtue of this arrangement, the bottom 10, proceeding from the expanded position of the socket inlay 5 shown in FIGS. 3 and 4a, can be pulled in the distal direction by means of the winch and thus pulled into the socket body 2. The socket inlay 5 in this case is turned back until it assumes the position shown in FIGS. 1 and 2.

Figure 3:
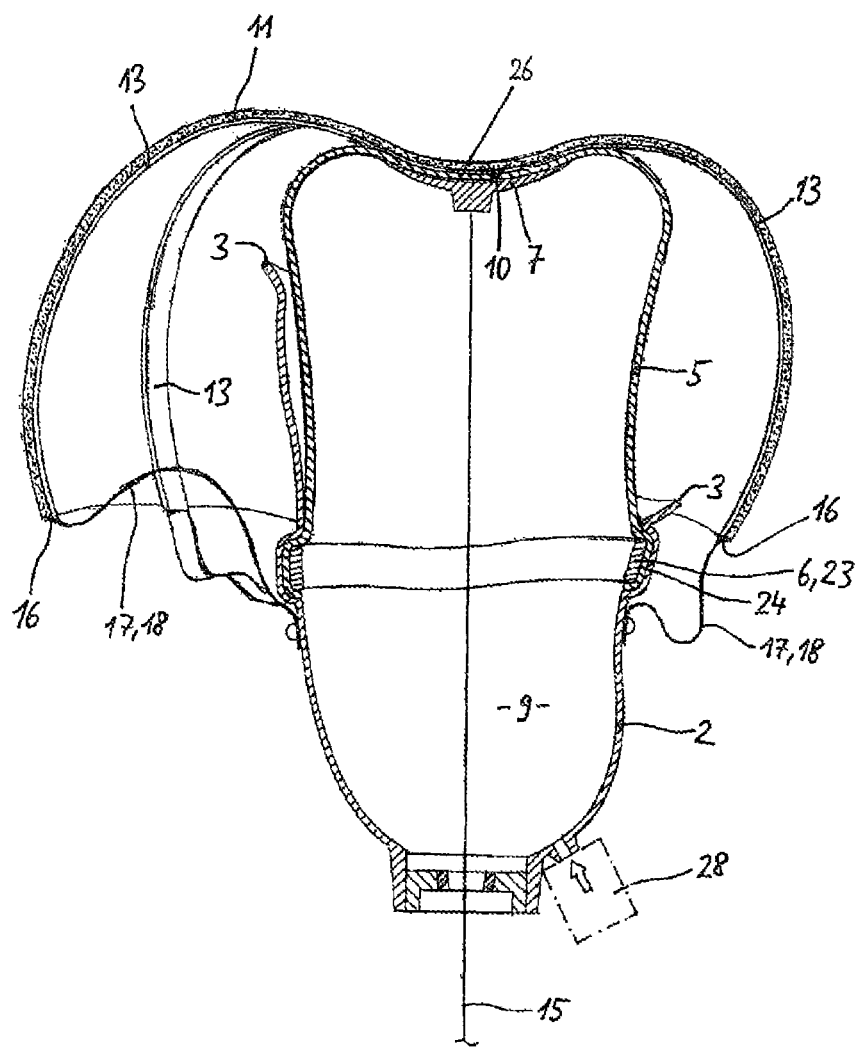
FIG. 3 shows a vertical section of the prosthesis socket, wherein the inlays are located in a pushed-out state.

As will be seen from FIGS. 1 to 3, the socket body 2 extends proximally beyond the socket entry plane 20, wherein the distance between the proximal socket edge 3 and the socket entry plane 20 varies. Moreover, the proximal socket edge 3 of the socket body 2 extends in an undulating manner. The edge profile is generally adapted individually to the patient. For example, in the prosthetic leg shown, the greater trochanter is completely enclosed laterally, whereas in the perineum a deep cut has to ensure enough space for the adductor tendon and ramus. Moreover, it would be disadvantageous to secure the socket inlay 5 along and in immediate proximity to the irregular proximal socket edge 3, since it would then not be possible to obtain a uniform, symmetrical and crease-free eversion of the socket inlay 5 along the stump insertion direction, and instead the socket inlay 5 would be turned out irregularly and obliquely. However, the fastening of the socket inlay 5 at a distal spacing from the proximal socket edge 3, as shown in the figures, has the consequence that the area of the socket body 2 between the socket entry plane 20 and the proximal socket edge 3 is no longer covered by the socket inlay 5. The skin of the amputation stump 19 would therefore bear on this uncovered proximal area of the socket body which, as a result of the high level of friction, may lead to pain caused by pulling of the skin and to a compression of the soft-tissue parts above the proximal edge 3. Moreover, the increased friction between the amputation stump and the socket body area lying above the socket entry plane 20 could have the result that it is not possible for the prosthesis socket 1 to be fully fitted.

To overcome this problem, the prosthesis socket 1 has an additional insertion aid, which facilitates the insertion of the amputation stump 19 into the socket body 2. The insertion aid comprises an additional inlay, which is designated here as insertion inlay 11. In its inner position, which is shown in FIGS. 1 and 2, the insertion inlay 11 completely lines the socket body 2, wherein it extends from the distal end of the socket body 2 to the proximal socket edge 3 or at least to a point near the proximal socket edge 3. The insertion inlay 11 thus covers both the socket inlay 5 and also that socket body area lying proximally with respect to the socket entry plane 20.

The insertion inlay 11 comprises an insertion stocking 12 and elastic, flexible, but non-buckling stretching elements 13, which are arranged on the outside of the insertion stocking 12, i.e. the side facing toward the socket body 2, and are firmly connected thereto. This connection can be provided, for example, by an adhesive layer 14 (see detail in FIG. 2).

The insertion stocking 12 can be produced, for example, from silicone, PU or copolymers or similar plastics. A material is expediently used which has good sliding properties at least on the side facing toward the socket body 2. It is also readily possible to coat the insertion stocking 12 on this side with a special sliding material.

The stretching elements 13 are elongate, easily flexible but non-buckling guide rods or slats that extend from the bottom 26 of the insertion inlay 11 or insertion stocking 12 (FIG. 2), in the longitudinal direction of the insertion stocking 12, as far as the proximal edge area 16 of the latter. Since the proximal edge profile of the insertion stocking 12 is adapted to the undulating proximal socket edge 3 of variable height and extends to the same height, the length of the stretching elements 13 arranged on both sides with respect to the longitudinal central axis of the prosthesis socket 1 is different depending on whether the corresponding stretching element 13 is arranged mainly medially, laterally, anteriorly or posteriorly. As will also be seen from FIGS. 1 to 3, a plurality of stretching elements 13 are arranged about the circumference of the insertion stocking 12, with eight stretching elements 13 being provided in the illustrative embodiment shown. However, this number can vary widely, for example between three and thirty. Preferably, the stretching elements 13 are arranged at least more or less uniformly about the circumference of the insertion stocking 12, such that they are at approximately the same distance from one another.

The entire insertion inlay 11, in the inner position, lies loosely inside the socket body 2 and is only secured in its proximal edge area 16 to a movable holding device 17 and, in the area of its bottom 26, to the bottom 10 of the socket inlay 11.

In order to prevent the insertion inlay 11 from moving or twisting in an undesired manner relative to the socket inlay 5 when the amputation stump 19 is inserted, the socket inlay 5 is preferably provided, on its side facing toward the insertion inlay 11, with a friction-increasing layer, in particular a silicone layer.

In the illustrative embodiment shown, the holding device 17 comprises several holding tapes 18 which are arranged about the circumference of the socket body 2 and which, in the inner position of the insertion inlay 11 shown in FIGS. 1 and 2, are guided at their proximal end slightly around the proximal socket edge 3 and are connected to the proximal edge area 16 of the insertion inlay 11, while they are otherwise guided distally outside the socket body 2 and are secured to the outside of the socket body 2 at their distal end, in a securing plane which lies parallel to the socket entry plane 20. In the illustrative embodiment shown, the securing of the distal ends of the holding tapes 18 is effected by means of rivets 25. Moreover, each stretching element 13 is secured on a holding tape 18. The length of the holding tapes 18 is dimensioned such that, in the inner position of the insertion inlay 11, they are tensioned or at least almost tensioned.

The holding device 17 thus forms an anchor for the proximal end area of the insertion inlay 11, wherein the anchor permits a certain radially outward movement of this proximal end area beyond the proximal socket edge 3, although this movement is limited to an extent that is defined by the length of the holding tapes 18.

The bottom 26 of the insertion inlay 11, i.e. the end area arranged distally in the inner position, is secured to the bottom 10 of the socket inlay 5. This securing can be effected by means of an adhesive, for example. However, the securing is limited exclusively to this distal end area 10, while the other areas of the insertion inlay 11 have no further fixed connection to the socket inlay 5.

When the socket inlay 5 is turned out from the inner position shown in FIG. 2 to the expanded position shown in FIG. 3, the edge area 16 of the insertion inlay 11 moves upward and radially outward beyond the proximal socket edge 3 and then, at a radial distance from the socket body 2, is pulled back down slightly, i.e. in the distal direction, by the holding tapes 18. Since the stretching elements 13 are flexible but resistant to buckling, the insertion inlay 11 is stretched out like an umbrella or mushroom. The stretching elements 13 thus act as guide struts for the insertion stocking 12. The insertion stocking 12, made of an elastic, extensible material, is stretched out, free of creases, by the spring force of the stretching elements 13, until the insertion stocking 12 does not stretch any further. When the socket inlay 5 is turned out farther to its maximum end position by the introduced fluid, as is shown in FIG. 3, the proximal edge area 16 of the insertion inlay 11 is pushed farther forward in the distal direction by means of the stretching elements 13, wherein the mushroom-like shape of the insertion inlay 11 is defined by the extension of the insertion stocking 12. In the end position, which is shown in FIG. 3, the holding tapes 18 can therefore be relaxed.

It will be seen from FIG. 3 that the bottom 26 of the insertion inlay 11, together with the bottom 10 of the socket inlay 5, is arranged uniformly perpendicularly with respect to the stump insertion direction, that is to say horizontally in FIG. 3.

Figure 4:
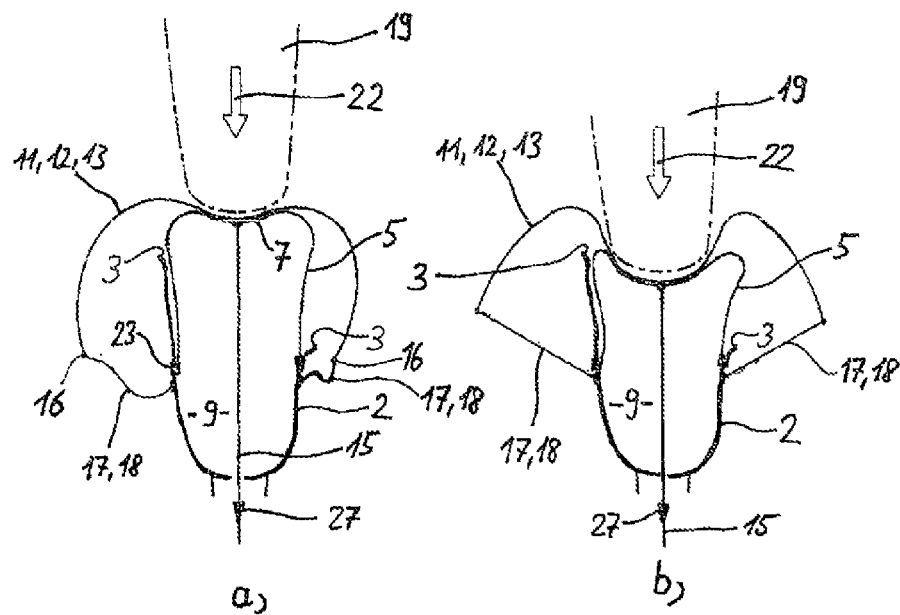
FIGS. 4*a*-4*d* show the prosthesis socket during the insertion of an amputation stump, wherein four different insertion positions are depicted.
Figure 4:
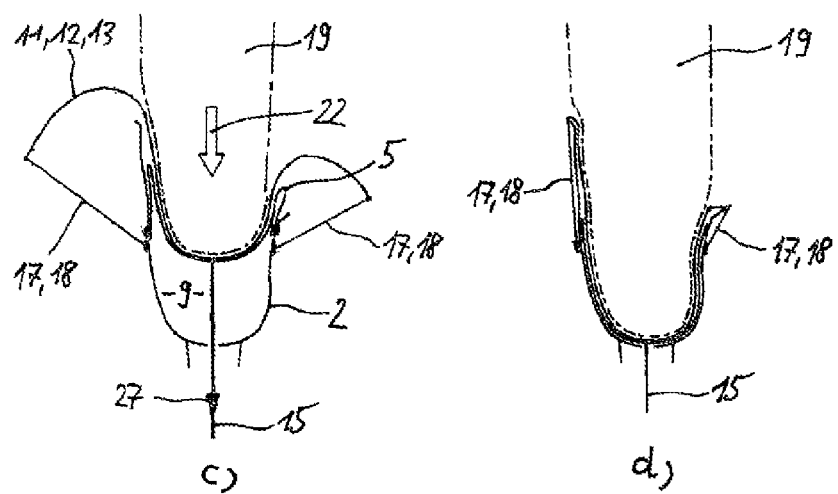

The insertion of the amputation stump 19 into the prosthesis socket 1 is explained in detail below with reference to FIG. 4.

FIG. 4a shows the expanded position of the socket inlay 5, this position corresponding to that in FIG. 3. It will be noted that the amputation stump 19 is first of all applied from above, in insertion direction 22, onto the bottom 26 of the insertion inlay 11 and therefore also onto the bottom 10 of the socket inlay 5. At the same time, a tensile force is applied by means of a winch (not shown) to the cable 15, as is indicated by the arrow 27.

By means of the cable 15, and by a certain but relatively low pressing force of the amputation stump 19, the socket inlay 5 and the insertion inlay 11 are then introduced together into the socket body 2, as can be seen from FIG. 4b. The stretching elements 13 of the insertion inlay 11 bend above the proximal socket edge 3 without buckling. By means of the holding tapes 18 being tensioned in the meantime, the edge area 16 of the insertion inlay 11 is guided in a circle formation about the distal securing points of the holding tapes 18.

When the amputation stump 19 is inserted farther into the prosthesis socket 1, as can be seen from FIG. 4c, the radial compression of the amputation stump 19 begins, since the prosthesis socket 1 has a smaller diameter than the amputation stump 19. By means of the cable 15, the bottom 10 of the socket inlay 5, and therefore also the bottom 26 of the insertion inlay 11, is pulled in increasingly in the distal direction, wherein the insertion inlay 11, during the entire insertion procedure, forms between amputation stump 19 and socket body 2 an intermediate layer that slides easily along the socket body 2.

In the position shown in FIG. 4d, the insertion inlay 11 is located in its inner position, in which it completely lines the socket body 2.

Many variations are possible within the context of the invention. For example, the insertion inlay 11 according to the invention can also be used without an additional socket inlay 5. The cable 15 is in this case secured to the bottom 26 of the insertion inlay 11 and can also be used to fix the insertion inlay 11 on the bottom of the socket body 2. Instead of using a winch, the cable 15 can also be actuated manually.

The invention claimed is:

1. A prosthesis socket, comprising:
   a socket body for receiving an amputation stump, the socket body having a proximal socket edge and a distal end area;
   a holding device fixed on the socket body;
   an insertion aid which facilitates insertion of the amputation stump into the socket body, the insertion aid comprising:
      an insertion inlay comprising:
         a proximal edge area connected to the holding device;
         a bottom end;
         an insertion stocking movable between an outer position, in which at least a portion of the insertion inlay is located outside the socket body, and an inner position, in which the insertion stocking lines the socket body with the proximal edge area positioned at the proximal socket edge of the socket body and with the bottom end positioned in the distal end area of the socket body;
         elastic, pressure-stable stretching elements which extend along the insertion stocking, are fixed on the insertion stocking, and are movable together with the insertion stocking.

2. The prosthesis socket as claimed in claim 1, wherein the holding device is movable relative to the proximal socket edge.

3. The prosthesis socket as claimed in claim 1, wherein the socket body has an outer wall, and the holding device is fixed on the outer wall.

4. The prosthesis socket as claimed in claim 1, wherein the socket body has an entry plane which lies perpendicular with respect to the stump insertion direction, and the holding device is fixed on the socket body at a height of or parallel to the socket entry plane.

5. The prosthesis socket as claimed in claim 1, wherein the holding device is composed of a plurality of holding tapes or cords arranged about a circumference of the socket body.

6. The prosthesis socket as claimed in claim 1, wherein the holding device comprises a hose-like holding member that surrounds the socket body.

7. The prosthesis socket as claimed in claim 5, wherein the holding device comprises a stretching element, and the holding tapes or cords are each secured on the stretching element.

8. The prosthesis socket as claimed in claim 1, wherein the insertion stocking comprises guide tabs or pockets, and the stretching elements comprise elongate, flexible guide rods or slats, which are firmly connected to the insertion stocking or are fitted in the guide tabs or pockets of the insertion stocking.

9. The prosthesis socket as claimed in claim 1, wherein a plurality of stretching elements are arranged about a circumference of the insertion stocking, the stretching elements being spaced apart by approximately identical spacing.

10. The prosthesis socket as claimed in claim 1, wherein the stretching elements extend from the bottom end of the insertion inlay to the proximal edge area of the insertion inlay.

11. The prosthesis socket as claimed in claim 1, wherein the insertion inlay, in its outer position, is inverted, and the bottom of the insertion inlay is located outside the socket body or at a same height as the proximal socket edge of the socket body.

12. The prosthesis socket as claimed in claim 1, further comprising a flexible socket inlay arranged between the insertion inlay, located in its inner position, and the socket body, the flexible socket inlay delimits, with or without the socket body, a fluid-tight fluid pressure chamber can be pushed out in a proximal direction by generation of an overpressure in the fluid pressure chamber, and has a bottom movable relative to the socket body.

13. The prosthesis socket as claimed in claim 12, wherein the insertion inlay is connected to the socket inlay at the bottom.

14. The prosthesis socket as claimed in claim 12, wherein the bottom of the socket inlay is designed as a dimensionally stable cap.

15. The prosthesis socket as claimed in claim 12, wherein the socket inlay is connected in a fluid-tight manner to the socket body in a socket entry plane that lies perpendicularly with respect to a stump insertion direction.

16. The prosthesis socket as claimed in claim 12, wherein the fluid pressure chamber is connectable, via a fluid channel routed through the socket body, to an overpressure generator which is secured on the socket body or which is arranged separately from the socket body.

17. The prosthesis socket as claimed in claim 1, wherein the stretching elements comprise plastic or spring steel.

18. The prosthesis socket as claimed in claim 1, further comprising at least one tensioning element configured to move a distal end of the insertion inlay in a direction toward a distal end of the socket body.

19. A prosthesis socket comprising:
a socket body configured to receive an amputation stump, the socket body having a proximal socket edge and a distal end area;
a holding device connected to the socket body;
an insertion aid configured to facilitate insertion of the amputation stump into the socket body, the insertion aid comprising:
an insertion inlay comprising:
a proximal edge area connected to the holding device;
a bottom end;
an insertion stocking movable between an outer position in which at least a portion of the insertion inlay is located outside the socket body and an inner position in which the insertion stocking lines the socket body with the proximal edge area positioned at the proximal socket edge of the socket body and with the bottom end positioned in the distal end area of the socket body;
elastic, pressure-stable stretching elements which extend along a length of the insertion stocking, are spaced apart around a perimeter of the insertion stocking, are fixed on the insertion stocking, and are movable together with the insertion stocking.

* * * * *